(12) United States Patent
Gibbs et al.

(10) Patent No.: US 11,013,850 B2
(45) Date of Patent: May 25, 2021

(54) COMPOSITE FLUID SEPARATION

(71) Applicant: Terumo BCT, Inc., Lakewood, CO (US)

(72) Inventors: Bruce W. Gibbs, Arvada, CO (US); Bruce Ellingboe, Littleton, CO (US); Jeffrey J. Blakeslee, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 258 days.

(21) Appl. No.: 15/830,870

(22) Filed: Dec. 4, 2017

(65) Prior Publication Data

US 2018/0154067 A1    Jun. 7, 2018

Related U.S. Application Data

(60) Provisional application No. 62/429,332, filed on Dec. 2, 2016.

(51) Int. Cl.
| | | |
|---|---|---|
| *A61M 1/36* | (2006.01) | |
| *A61M 1/02* | (2006.01) | |
| *B04B 13/00* | (2006.01) | |
| *B04B 5/04* | (2006.01) | |
| *A61M 1/38* | (2006.01) | |

(52) U.S. Cl.
CPC .......... *A61M 1/3696* (2014.02); *A61M 1/029* (2013.01); *A61M 1/0209* (2013.01); *A61M 1/3698* (2014.02); *A61M 1/382* (2013.01); *B04B 5/0442* (2013.01); *B04B 13/00* (2013.01); *A61M 2202/0415* (2013.01); *A61M 2202/0427* (2013.01); *A61M 2202/0439* (2013.01); *A61M 2205/3365* (2013.01); *A61M 2205/50* (2013.01); *B04B 2005/0471* (2013.01)

(58) Field of Classification Search
None
See application file for complete search history.

(56) References Cited

U.S. PATENT DOCUMENTS

| | | | |
|---|---|---|---|
| 4,187,979 A * | 2/1980 | Cullis ................. | A61M 1/3693 494/1 |
| 6,348,031 B1 | 2/2002 | Unger et al. | |
| 6,740,239 B2 | 5/2004 | Högberg et al. | |
| 6,994,790 B2 | 2/2006 | Corbin, III et al. | |
| 7,033,512 B2 | 4/2006 | Hlavinka et al. | |

(Continued)

FOREIGN PATENT DOCUMENTS

| | | |
|---|---|---|
| EP | 0438520 A1 | 7/1991 |
| JP | 2017169817 A | 9/2017 |
| JP | 2017169982 A | 9/2017 |

OTHER PUBLICATIONS

International Searching Authority, International Search Report and Written Opinion, dated Apr. 9, 2018, 20 pages.

(Continued)

*Primary Examiner* — Paul S Hyun
(74) *Attorney, Agent, or Firm* — Terumo BCT, Inc. IP Law Department

(57) ABSTRACT

Embodiments are described that include systems and methods for separating components of a composite fluid, e.g., whole blood. Some embodiments provide for processing a composite fluid by subjecting a volume of the fluid to a first centripetal acceleration for an initial separation, followed by a second centripetal acceleration for a second separation.

14 Claims, 10 Drawing Sheets

(56) References Cited

U.S. PATENT DOCUMENTS

| | | |
|---|---|---|
| 7,235,041 B2 | 6/2007 | Högberg et al. |
| 7,279,107 B2 | 10/2007 | Högberg et al. |
| 7,347,932 B2 | 3/2008 | Holmes et al. |
| 7,396,451 B2 | 7/2008 | Holmes et al. |
| 7,438,679 B2 | 10/2008 | Hlavinka et al. |
| 7,674,221 B2 | 3/2010 | Hudock et al. |
| 7,766,809 B2 | 8/2010 | Dolecek et al. |
| 7,819,793 B2 | 10/2010 | Lindell et al. |
| 7,833,185 B2 | 11/2010 | Felt et al. |
| 7,964,048 B2 | 6/2011 | Hlavinka et al. |
| 7,981,019 B2 | 7/2011 | Holmes et al. |
| 8,016,736 B2 | 9/2011 | Hlavinka et al. |
| 8,057,377 B2 | 11/2011 | Holmes et al. |
| 8,120,760 B2 | 2/2012 | Stanton et al. |
| 8,173,027 B2 | 5/2012 | Hogberg et al. |
| 8,236,184 B2 | 8/2012 | Holmes et al. |
| 8,277,406 B2 | 10/2012 | Felt et al. |
| 8,337,380 B2 | 12/2012 | Ellingboe et al. |
| 8,366,086 B2 | 2/2013 | Bucciaglia et al. |
| 8,425,448 B2 | 4/2013 | Felt et al. |
| 8,439,889 B2 | 5/2013 | Sano |
| 8,460,267 B2 | 6/2013 | Hirabuki |
| 8,800,881 B2 | 8/2014 | Biset et al. |
| 8,840,535 B2 | 9/2014 | Dolecek |
| 8,870,734 B2 | 10/2014 | Eberle et al. |
| 8,900,112 B2 | 12/2014 | Holmes et al. |
| 8,944,983 B2 | 2/2015 | Nguyen et al. |
| 8,992,403 B2 | 3/2015 | Eberle et al. |
| 9,028,388 B2 | 5/2015 | Dolecek et al. |
| 9,060,920 B2 | 6/2015 | Hirabuki |
| D734,487 S | 7/2015 | Ellingboe et al. |
| 9,079,194 B2 | 7/2015 | Hlavinka et al. |
| 9,132,949 B2 | 9/2015 | Bidet et al. |
| 9,242,252 B2 | 1/2016 | Eberle et al. |
| 9,375,729 B2 | 6/2016 | Eberle et al. |
| 9,579,447 B2 | 2/2017 | Hirabuki et al. |
| 9,733,805 B2 | 8/2017 | Diaz et al. |
| 9,820,912 B2 | 11/2017 | Imai |
| 9,839,729 B2 | 12/2017 | Biset et al. |
| 9,839,730 B2 | 12/2017 | Biset et al. |
| 2002/0020680 A1 | 2/2002 | Jorgensen |
| 2006/0205581 A1 | 9/2006 | Chammas |
| 2007/0209708 A1 | 9/2007 | Hermann et al. |
| 2011/0003675 A1 | 1/2011 | Dolecek |
| 2011/0053201 A1 | 3/2011 | Eberle et al. |
| 2011/0136650 A1 | 6/2011 | Ellingboe et al. |
| 2011/0294641 A1 | 12/2011 | Dolecek et al. |
| 2013/0153482 A1 | 6/2013 | Gibbs et al. |
| 2014/0070122 A1 | 3/2014 | Imai et al. |
| 2015/0140546 A1 | 5/2015 | James et al. |
| 2016/0046410 A1 | 2/2016 | Nakamura |
| 2016/0243300 A1 | 8/2016 | Nackaerts |
| 2016/0317727 A1 | 11/2016 | Hirabuki et al. |
| 2017/0043071 A1 | 2/2017 | Imai |

OTHER PUBLICATIONS

International Seraching Authority, International Preliminary Report on Patentability, PCT/US2016/01877 dated Aug. 31, 2017, 9 pages.
International Seraching Authority, International Search Report, PCT/US2016/01877 dated May 12, 2016, 3 pages.
International Searching Authority; International Preliminary Report on Patentability, PCT/2017/064548, dated Jun. 13, 2019, 16 pages.

\* cited by examiner

COMPOSITE FLUID SEPARATION

CROSS-REFERENCE TO RELATED PATENT APPLICATION(S)

This patent application claims priority to U.S. Provisional Patent Application No. 62/429,332 filed Dec. 2, 2016 entitled "COMPOSITE FLUID SEPARATION," which is hereby incorporated by reference in its entirety as if set forth herein in full.

BACKGROUND

There are many composite fluids including biological fluids that are separated into components. The components may then be utilized after separation. One example of a biological fluid that is separated into components is whole blood. Conventionally, whole blood obtained by blood donations is separated into its components such as red blood cells, white blood cells, platelets, and plasma. The components may be individually transfused into a patient. It is believed that component transfusion, instead of transfusion of whole blood, may lessen the burden on a patient's circulatory system and reduce possible side effects of transfusion.

Whole blood obtained by blood donation may be centrifuged to separate the whole blood into its components. For example, the whole blood may be separated into a plasma fraction, a red blood cell fraction, a platelet fraction, and a white blood cell fraction. In some situations, it may be desirable to maximize the amount of platelets and plasma that are recovered from a single unit of whole blood.

Embodiments of the present invention have been made in light of these and other considerations. However, the relatively specific problems discussed above do not limit the applicability of the embodiments.

SUMMARY

The summary is provided to introduce aspects of some embodiments of the present invention in a simplified form, and is not intended to identify key or essential elements of the claimed invention, nor is it intended to limit the scope of the claims.

Embodiments provide for separation units that hold bag systems. The separation units and bag systems may be used with a centrifuge apparatus to separate a composite liquid into components. In some embodiments, the composite liquid may be whole blood.

Embodiments also provide methods of separating composite fluids, e.g., liquids, into components. Methods may provide for subjecting a volume of liquid that includes at least a first component, a second component, and a third component to a first centripetal acceleration. The volume of liquid may be separated into parts and/or components, which may make up the parts. At least a first part, which may include one or more components may be transferred from a first chamber to a second chamber. The volume of liquid (including the transferred parts) may then be subjected to a second centripetal acceleration. In embodiments, the second centripetal acceleration may be greater than the first centripetal acceleration. A portion of the first component may then be transferred out of the second chamber. An additional portion of the first component may be transferred out of the first chamber.

BRIEF DESCRIPTION OF THE DRAWINGS

Non-limiting and non-exhaustive embodiments are described with reference to the following figures.

DETAILED DESCRIPTION

Figure 1:
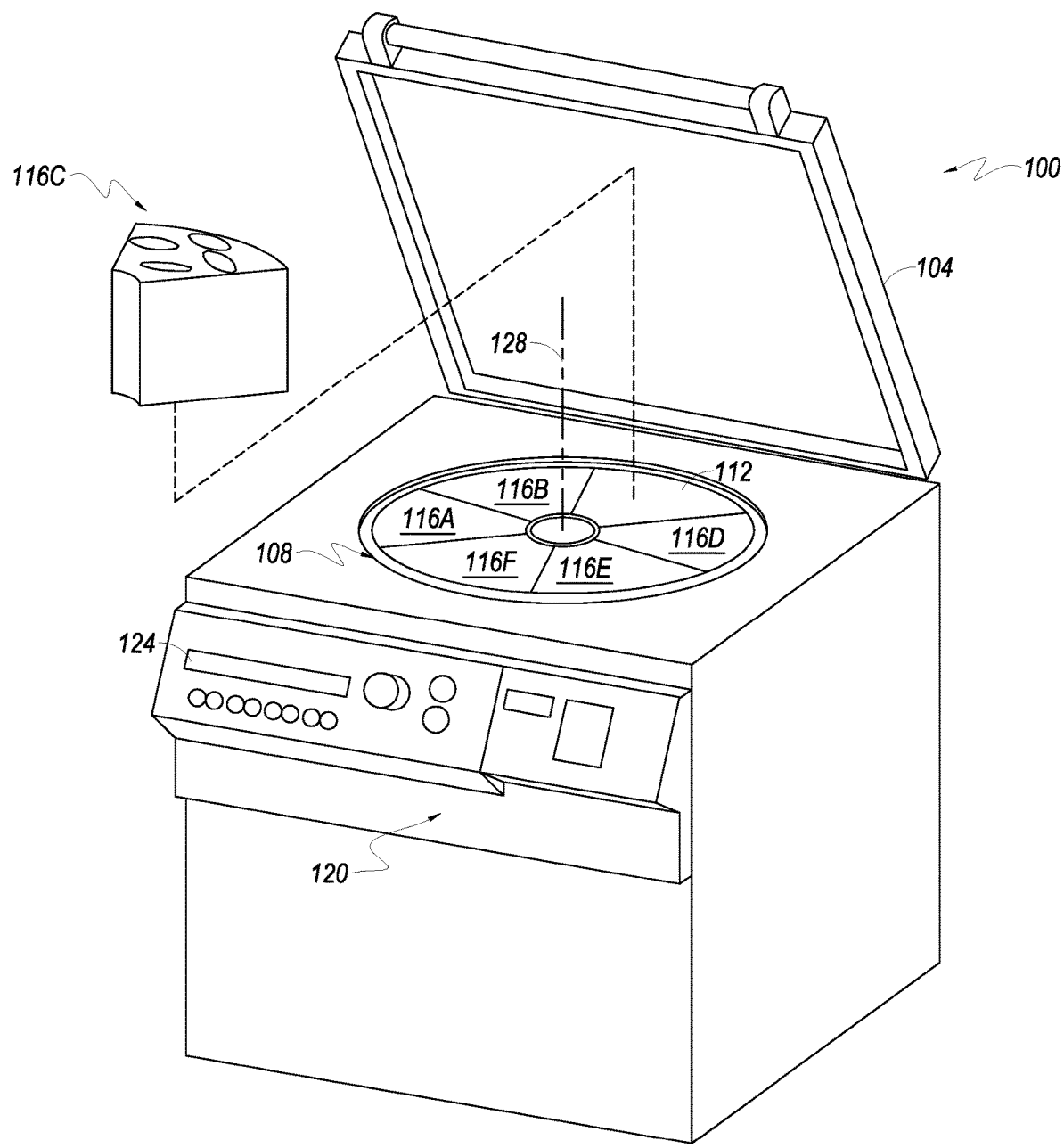
FIG. 1 illustrates a perspective view of a centrifuge apparatus for separating blood according to one embodiment.

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Some embodiments of the present disclosure may provide for ease of loading a disposable into a whole blood automation device by creating a "top/top" system. In other words, blood and blood component expression may be out the top of a whole blood collection bag.

In embodiments where a "top/top" type system design may not yield enough plasma or platelets, or has too much cellular contamination of plasma, then the system may be designed and used as follows:

A bag, with a volume of whole blood, may be placed into a centrifuge chamber which has a means of expressing blood out of the bag (e.g., an active chamber). The platelet bag may be loaded into a second active chamber. The remaining bags may be loaded into a third chamber. Valves may be arranged (valve to valve) and seal between the various bags, and sensors to monitor the clarity of the fluid in the tubing running through it. The bags may be loaded, tubing loaded into sensors and valves, clamps closed, and any seals, frangibles, cliktips, etc. opened to the whole blood container. This opening of seals, frangibles, cliktps, etc. may be done automatically The centrifuge chamber may be spun after opening all valves so that air is drawn from all bags. A soft spin that separates the platelets and plasma (PRP) from red blood cell (RBC) product may be performed. Air may be expressed from the whole blood bag to the leukopack (white blood cell) bag. This PRP product may be expressed to a second chamber while spinning. The PRP product expression may be stopped according to signals from a sensor at the outlet of the processing bag and/or at inlet to platelet bag.

The relative position of the two active chambers may be determined by a G force that may be needed to recover the most plasma and keep it clear of cells. The centrifuge speed may be ramped up and maintained so as to recover additional plasma (and possibly platelets) and sediment platelets out of the plasma. The plasma from this second active chamber may be expressed, and ended, based on a sensor.

Additional plasma volume may be expressed from the platelet bag if it is known that the platelet yield is poor. This assessment may be made from sensor signals during the expression of the PRP product. Additional plasma (and perhaps platelets) may be expressed from the whole blood bag/active chamber. This expression may also be controlled by a sensor monitoring tubing by the bag. Then a residual leukocyte (white blood cell) layer may be expressed from the remaining RBC product in order to make a leuko-poor RBC product.

Reference will now be made in detail to the embodiments illustrated in the accompanying drawings and described below. Wherever possible, the same reference numbers are used in the drawings and the description to refer to the same or like parts. Although the description below may be made with respect to the separation of blood, embodiments may be used in separating components from any composite fluid, e.g., biological liquids, organic liquids, inorganic liquids, and/or fluidized solids.

An embodiment of a centrifuge apparatus 100 is shown in FIG. 1. Centrifuge apparatus 100 may be box-shaped, and may include an openable/closable cover 104 at the top, means for centrifuging (e.g., a centrifugal drum 108) in the inside, six unit insertion holes 112 provided at regular angular intervals inside the centrifugal drum 108, and six separation units 116A-F inserted in respective ones of the unit insertion holes 112. In other embodiments, the apparatus 100 may include less than six separation units and insertion holes, or more than six separation units and insertion holes. The apparatus 100 may be operated based on user interface (UI) controls on a console section 120 provided at the front of apparatus 100, which may be controlled by a computer (e.g., computer system 900 (FIG. 9)), and may be configured to display predetermined information on a display 124.

In embodiments, a bag system (a system of disposable bags and tubing connecting the bags, e.g., bag system 400 (FIG. 4)) that includes a composite fluid such as whole blood, may be loaded into a separation unit such as separation unit 116C, which may be installed in centrifuge apparatus 100. Each separation unit may have chambers and features that allow the tubing and bags to be positioned in the separation unit. Examples of some features (e.g., chambers) of various separation units are described in greater detail below (FIGS. 2, 3, 5, and 6). A separation unit may be permanently installed in apparatus 100 before the bag system is loaded onto the separation unit. In other embodiments, the separation unit may not be installed in the apparatus 100. That is, it may be removed from the apparatus 100 to load a bag system, and may be reinstalled in the apparatus 100 after the bag system is loaded onto the separation unit.

It is noted that although the separation unit 116C is shown with a particular shape, in other embodiments (such as the ones described below) the shape may be different and correspond to the shape of unit insertion holes in the apparatus.

In the embodiment of FIG. 1, apparatus 100 has six slots where six separation units 116A-F may be positioned in apparatus 100. In embodiments, separation units 116A-F are installed in apparatus 100. Six bag systems may then be loaded into apparatus 100 with one bag system being loaded into each of separation units 116A-F. Each of the bag systems mounted into separation units 116A-F may include a bag with a volume of composite fluid, e.g., whole blood. Apparatus 100 may create centripetal acceleration by spinning centrifugal drum 108 and separation units 116A-F around the axis of rotation 128. The centripetal acceleration may then separate the volumes of composite fluid loaded in the separation units 116A-F into components, e.g., whole blood into, plasma, platelets, white blood cells, and red blood cells. As may be appreciated, the centripetal acceleration may increase in apparatus 100 as you move away from the axis of rotation 128. Also, a stronger centripetal acceleration may be created by spinning the centrifuge at a greater RPM (rotations per minute).

Figure 2:
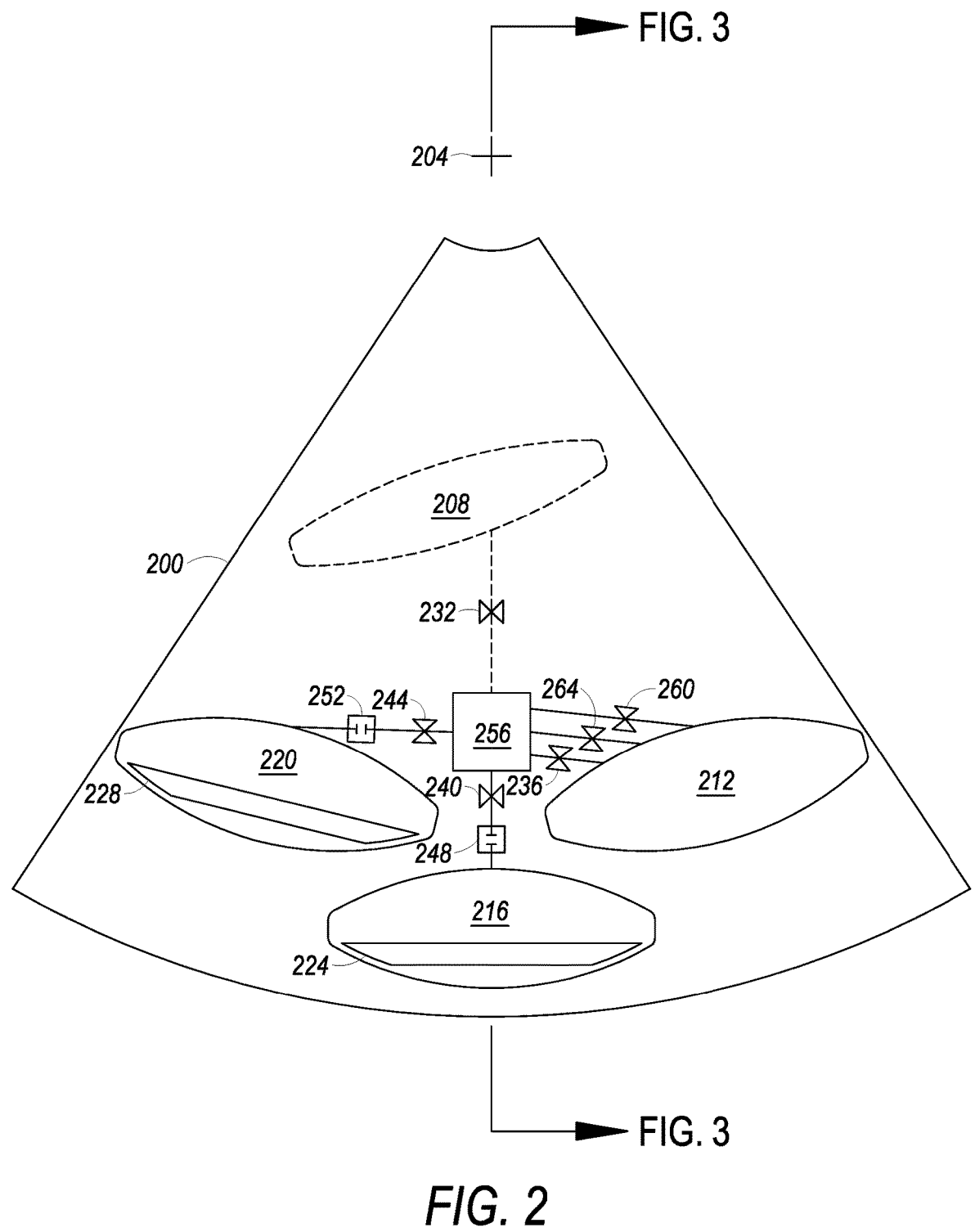
FIG. 2 illustrates a top view of a separation unit according to an embodiment.

FIG. 2 illustrates a top view of a separation unit 200. In embodiments, separation unit 200 may be one of many (e.g., a plurality of) separation units installed in a centrifuge apparatus, e.g., apparatus 100. When installed in a centrifuge apparatus, separation unit 200 may be rotated about axis of rotation 204. In the embodiment shown in FIG. 2, separation unit 200 includes three chambers (212, 216, and 220) and an optional fourth chamber 208, which may be used in some embodiments. Chambers 208, 212, 216, and 220 may have elliptical shaped cross-sections (taken on a plane perpendicular to axis 204). In other embodiments, the chambers may have a rectangular shaped cross section (taken on a plane perpendicular to axis 204). In other embodiments, the chambers may have any shape that accommodates containers, such as bags from a bag system (e.g., bag system 400 shown in FIG. 4).

Expressor 224 may assist in transferring liquid to and from chamber 216 and expressor 228 may assist in transferring liquid to and from chamber 220. Expressors used in the present embodiments may utilize any appropriate devices and/or systems that effect transfer of a fluid from one chamber to another. For example, an expressor may be operated using systems such as electromechanical, hydraulic, pneumatic, vacuum, centrifugal, or combinations of these types of systems. Expressors may include plates, screws, bladders, cylinders, pistons, balloons, etc. As one example, expressors may be hydraulic and include a bladder that is filled with hydraulic fluid. When the bladder is filled, it may press against a bag and express components from the bag and/or chamber to a different bag and/or chamber. When hydraulic fluid is removed from the bladder, negative pressure may be created, which may cause components to flow into a chamber.

Separation unit 200 also may include valves 232 (optional), 236, 240, 244, 260, and 264. The valves may be any type of appropriate valve, one non-limiting example including pinch valves. It is noted that although several valves are provided in unit 200, this is done merely for illustrative purposes. Other embodiments may provide for more, or less, valves. For example, one embodiment may provide for use of only four valves. Sensors 248 and 252 may be used to detect the various components of the composite fluid. For example, sensors 248 and 252 may be used to help determine when to stop transferring components from one or more chambers, e.g., when a different component is detected. A recess 256 may also be included in separation unit 200 to hold a coupling or manifold that may be part of a bag system mounted in separation unit 200.

Figure 3:
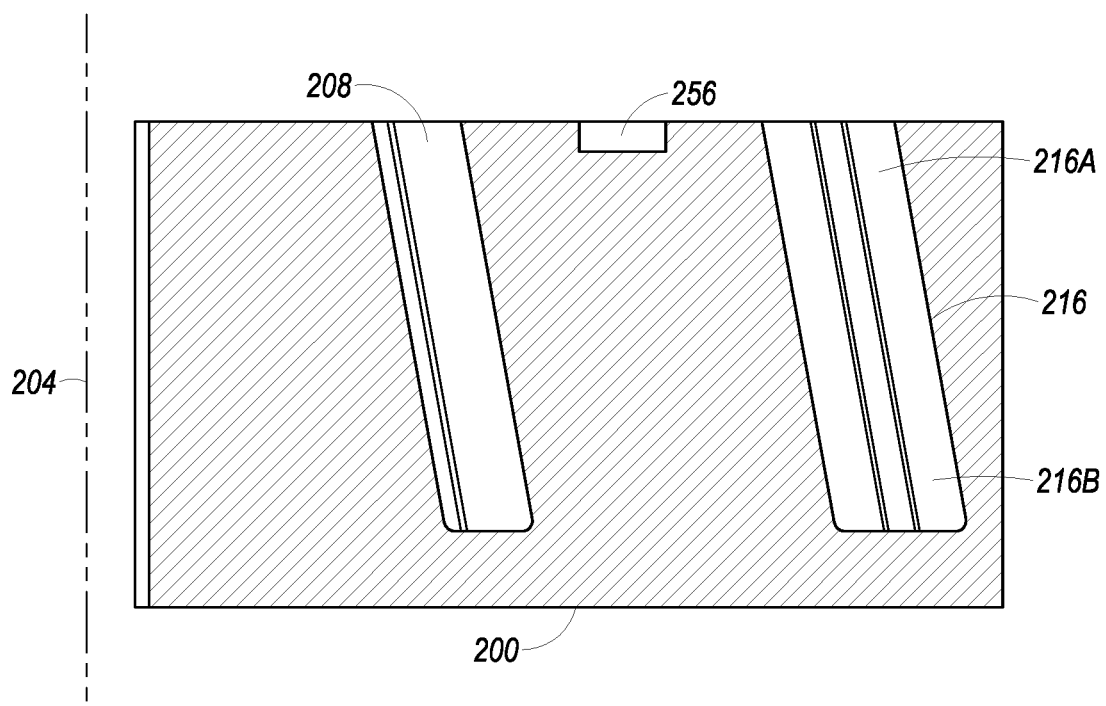
FIG. 3 illustrates a cross-sectional view of a separation unit according to an embodiment.

FIG. 3 illustrates a cross-sectional view of one embodiment of unit 200 showing a shape/design of chamber(s) 208 and 216. FIG. 3 illustrates features of chamber 216. In some embodiments, chambers 208, 212, 216, and 220 may have similar features. As shown in FIG. 3, chamber 216 includes a proximal end 216A and a distal end 216B.

In the embodiment shown in FIG. 3, chamber 216 is designed so that the distal end 216B is further away from the axis of rotation 204 than proximal end 216A. That is, chamber 216 is not generally parallel to axis 204. Rather, chamber 216 is slanted with respect to axis 204. In embodiments, all of chambers 208, 212, 216, and 220 may have features similar to chamber 216, namely, they may be slanted with respect to axis 204. In these embodiments, when unit 200 is spun around axis 204, larger and/or denser particles in chamber 216 (e.g., in a bag in chamber 216) may settle near distal end 216B, with lighter components settling near proximal end 216A.

Figure 4:
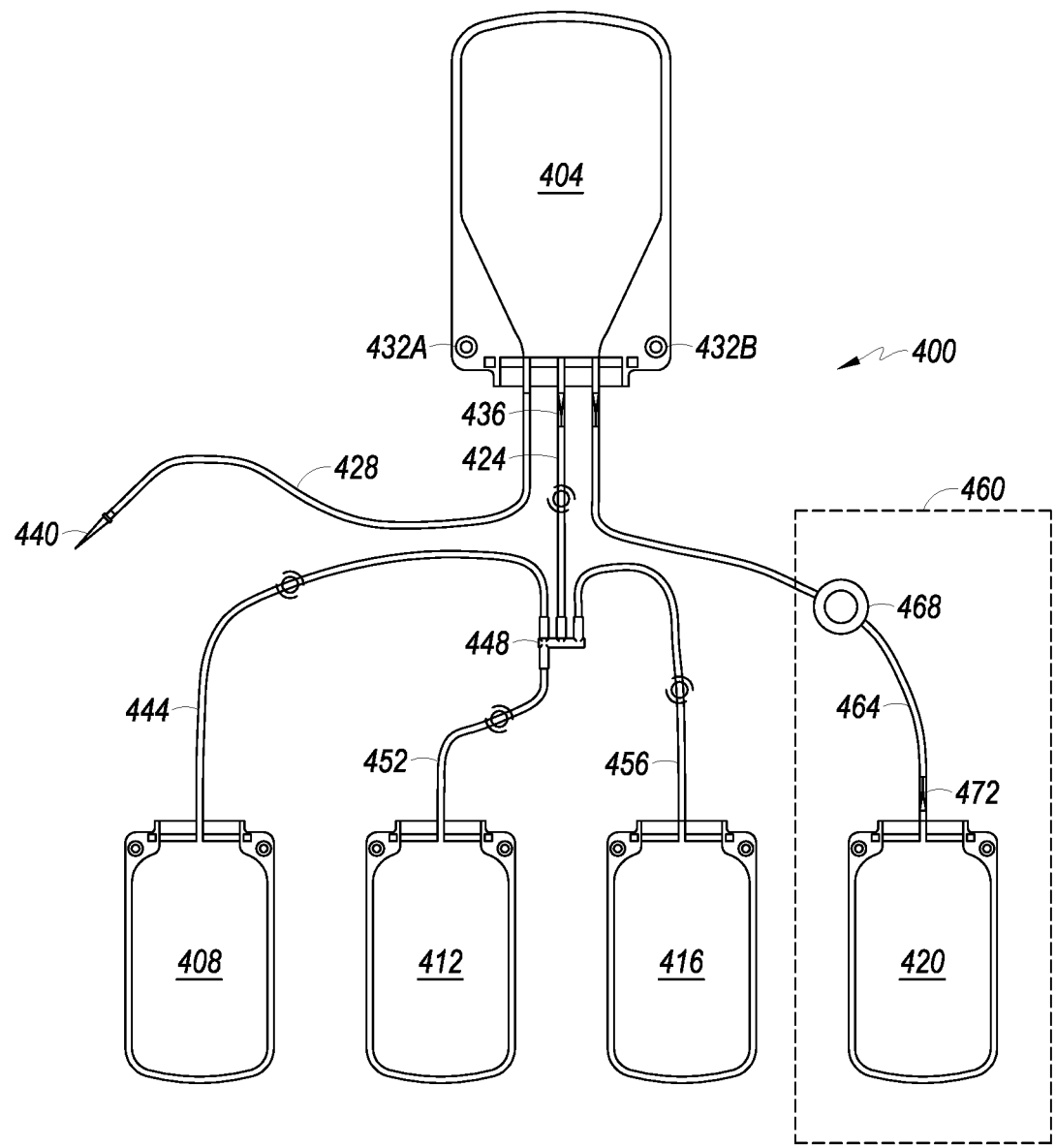
FIG. 4 illustrates a bag system that may be used with embodiments.

FIG. 4 shows an example of a bag system 400 that may be used, in embodiments, for the separation of a composite fluid (e.g. whole blood) into components (e.g. plasma, platelets, red blood cells, white blood cells, etc.). In embodiments, a bag system similar to bag system 400 may be loaded onto a separation unit, such as separation unit 200, for separating a composite liquid into components.

As shown in FIG. 4, bag system 400 comprises a separation bag 404 and at least three component bags 408, 412, and 416 connected thereto. In the embodiment shown in FIG. 4, system 400 also includes a fourth component bag 420.

In embodiments, bag 404 may be used as a collection bag for collecting the composite fluid (e.g., whole blood) and as a separation bag. For example, a volume of whole blood from a donor (e.g., about 450 ml) may be collected in bag 404. The bag 404 may be flat and generally rectangular. In embodiments, bag 404 may be made of two sheets of plastic material that may be welded together to define there between an interior space having a main rectangular portion connected to a triangular proximal portion.

A first tube 424 may be connected to a proximal end of the triangular portion of bag 404 and a second tube 428 may be connected adjacent the first tube 424. The proximal ends of tubes 424 and 428 may be connected to bag 404 by being embedded between the two sheets of plastic material. The separation bag 404 may further include holes 432A and 432B in each of its two proximal corners. The holes 432A and 432B may be used to secure the separation bag to a separation unit, such as separation unit 200.

Bag 404 may, in embodiments, initially contain a volume of anti-coagulant solution (e.g., about 63 ml of a solution of citrate phosphate dextrose for a blood donation of about 450 ml). Tube 424 may include, e.g., at its proximal end, a breakable stopper 436 respectively, blocking liquid flow there through. The breakable stopper 436 may in embodiments be implemented by a frangible.

The second tube 428 may be a collection tube for collecting a composite fluid (e.g., whole blood). A needle 440 may be connected to a distal end of the second tube 428. The needle 440 may for example be inserted in the vein of a donor to allow blood to flow into bag 404. After a desired volume of blood has been collected in the bag 404, the collection tube 428 may be sealed and cut, disconnecting the needle from bag system 400. Alternatively, previously collected blood may be transferred to bag 404 through tube 428, with or without the use of the needle 440.

In embodiments, bag 408 may be used to collect a component of the composite fluid after separation. For example, a plasma component separated from whole blood may be collected in bag 408. Bag 408 may be similarly constructed as bag 404 and may be flat and substantially rectangular. It may be connected through a tube 444 and a manifold or coupling (448) to tube 424. In some embodiments, the manifold or coupling may have a different shape than shown in FIG. 4. The second component bag 412 may be used for receiving a platelet component, in embodiments. The second component bag 412 may also be flat and substantially rectangular. It may be connected through a platelet collection tube 452 and the manifold 448 to the first tube 424. A third component bag 416 may receive a white blood cell component from the primary bag 404. Bag 416 may be connected through a white blood cell collection tube 456 and the manifold 448 to the first tube 424.

In some embodiments, system 400 may include an optional sub-system 460 for collecting and storing red blood cells. System 460 may be used by having the red blood cells drain from bag 404 through tube 464, which may include a filter 468 (e.g., leukocyte reduction filter), into third component bag 420. A breakable stopper 472 (e.g., frangible) in tube 464 prevents premature flow of red blood cells into the third component bag 420. In other embodiments, sub-system 460 may not be included in system 400. In these embodiments, the red blood cells may remain in bag 404, after separation and removal of the other components.

In some embodiments, the bag system may include an additional filter (e.g., leukocyte reduction filter). In these embodiments, the additional filter may be positioned between bag 404 and 408, such as in line with tube 444. The additional filter may be used to filter leukocytes from platelets before storing in bag 408.

Referring to FIGS. 2-4, in embodiments, system 400 may be loaded into separation unit 200. For example, bag 404 may be positioned in chamber 216, bag 412 may be positioned in chamber 220, and bags, 408, 416 and 420 may be positioned in chamber 212. In some embodiments, unit 200 may include a fourth chamber 208, where bag 416 may be positioned. In one embodiment, system 400 and unit 200 may be used to separate a unit (a predetermined volume, e.g., from about 250 to about 650 ml, such as about 500 ml) of whole blood, stored in bag 404, into components. In other embodiments, the volume may be as small as 200 ml or as large as 700 ml.

In embodiments, the fluids and components may flow into and out of chambers 208, 212, 216, and 220 through the top of the chambers. In other words, the bag systems may be loaded into the chambers from the top so that as fluid flows through tubes 424, 444, 452, 456, and 464, it flows into and out of the chambers through the top of the chambers. In embodiments, this may provide easy and convenient loading as it may require an operator to simply place the bags of a bag system (e.g., bag system 400) into the chambers without special routing of the tubes.

After system 400 has been loaded into unit 200, unit 200 is spun around axis of rotation 204 to create centripetal acceleration. For example, unit 200 may be in an apparatus such as centrifuge apparatus 100 that spins unit 200. The force created by the centripetal acceleration may be greater the further away from axis 204. Accordingly, in FIG. 2, chamber 216 may experience the largest force, followed by chamber 220, chamber 212, and finally chamber 208, which may experience the least amount of force. Also, as may be appreciated, the centripetal acceleration may increase with the speed of rotation of unit 200 around axis 204.

After system 400 is loaded into unit 200, unit 200 may be spun around axis of rotation 204 at a first speed to create a first centripetal acceleration. The first centripetal acceleration may effect the separation of whole blood in chamber 216 into components. For example, based on the differences in size and/or density, the blood may be separated in bag 404 (while in chamber 216) into red blood cells, white blood cells, and a plasma/platelet portion. As noted above, in embodiments, chamber 216 may be slanted or angled with respect to axis 204 (see FIG. 3). The distal end of chamber 216B may be further away from the axis of rotation 204 than the proximal end 216A. As a result of the shape of chamber 216 and the centripetal acceleration created by spinning unit 200 around axis 204, red blood cells may be at a bottom of bag 404, with a layer of white blood cells above the red blood cells, and a layer of platelets/plasma above the layer of white blood cells. That is, the platelets/plasma layer may be at the top.

After the initial separation, valve 240 and 244 may be opened and expressor 224 may be activated (e.g., by one or more processors of a computer system) to express the platelets/plasma layer out of chamber 216 (and out of bag 404). In embodiments, the platelets/plasma may be expressed from chamber 216 into chamber 220 (and into bag 412). The expression may move a first portion of the plasma (with the platelets) from chamber 216 into chamber 220. It is noted that some portion of plasma may remain in chamber 216. Sensors 248 and 252 may be used to determine when to stop expressing the platelets/plasma from chamber 216. For example, one or more of sensors 248 and 252 may sense the platelets/plasma as it flows from chamber 216 (e.g., and bag 406) to chamber 220 (e.g., into bag 412) and when the presence of white blood cells is sensed, the expressor 224 may be deactivated and valves 240 and 244 closed. In embodiments, the platelets/plasma may be referred to as platelet rich plasma (PRP).

After the platelets/plasma are expressed into chamber 220 (e.g., into bag 412), valves 240 and 244 may be closed and the unit 200 may be spun at a second speed, to create a second centripetal acceleration. It is noted that in embodiments, the unit 200 may be continuously spun throughout the process. In other words, rotating the unit 200 at the second speed may simply involve increasing the speed from a speed at which the unit 200 is already rotating. In embodiments, the second centripetal acceleration may be greater than the first centripetal acceleration. In other embodiments, the second centripetal acceleration may be substantially the same as the first centripetal acceleration. However, in yet other embodiments, the second centripetal acceleration may be less than the centripetal acceleration. As may be appreciated, the centripetal acceleration may be controlled by how fast the unit 200 is spun around axis of rotation 204.

The second spin may separate the platelets from the plasma in bag 412 (e.g., in chamber 220). Because of the size and density difference, the platelets may settle toward a bottom of chamber 220 with the plasma on top of the platelets. Also, in chamber 216 (and in bag 404), the second spin may separate additional plasma from the red blood cells and white blood cells. Again, because of density difference, the plasma may be on top of the red blood cells and white blood cells.

After the second spin, valves 244 and 236 may be opened and expressor 228 may be activated to express a second portion of plasma from chamber 220 (and bag 412) into chamber 212 (and into bag 408). Sensor 252 may be used to determine when to stop expressing the plasma layer from chamber 220. For example, sensor 252 may sense the plasma as it flows from chamber 220 to chamber 212 and when the presence of platelets is sensed, the expressor 228 may be deactivated and valves 244 and 236 closed.

Additionally, expressor 224 may be activated, and valve 240 opened, to express a third portion of plasma (separated by the second spin) from chamber 216 to chamber 212. In embodiments, this provides a larger volume of plasma (in bag 408) than may be conventionally collected from a unit (e.g., a predetermined volume) of whole blood. As may be appreciated, the second spin allows additional plasma to be separated from the red blood cells and white blood cells. Also, the fact that less plasma remains with the platelets, may result in a higher quality platelet product; having less plasma in the platelets, may reduce transfusion reactions that may result from plasma protein(s) transfused into patients with platelets.

After the third portion of plasma is removed from chamber 216 (and bag 404), valves 240 and 264 may be opened and expressor 224 may be activated to express the layer of white blood cells from chamber 216 (and bag 404) into chamber 212 (and into bag 416). In embodiments that include chamber 208, the white blood cells may be expressed into bag 416, which may be in chamber 208. In these embodiments, valve 232 may be opened instead of valve 264. Sensor 248 may be used to determine when to stop expressing the white blood cells from chamber 216. Sensor 248 may sense the white blood cells as they flow from chamber 216 to chamber 208 and when the presence of red blood cells is sensed, the expressor 224 may be deactivated and valves 240 and 232 closed.

Finally, in those embodiments that include sub-system 460, valves 240 and 260 may be opened and expressor 224 may be activated to express the red blood cells from chamber 216 (and bag 404) through filter 468 and into bag 420 (e.g., in chamber 212). Once all of the red blood cells have been expressed out of bag 404, valves 240 and 260 may be closed and the expressor 224 may be deactivated.

The description above is provided for illustrative purposes. Embodiments are not limited thereto. For example, as described below, embodiments provide for use of separation units with different features (e.g., units 500 and 600) that provide for different steps to be performed in separating components from fluids. Also, embodiments provide for separating different types of fluids, besides whole blood, including different biological fluids, organic fluids, and inorganic fluids.

Figure 5A:
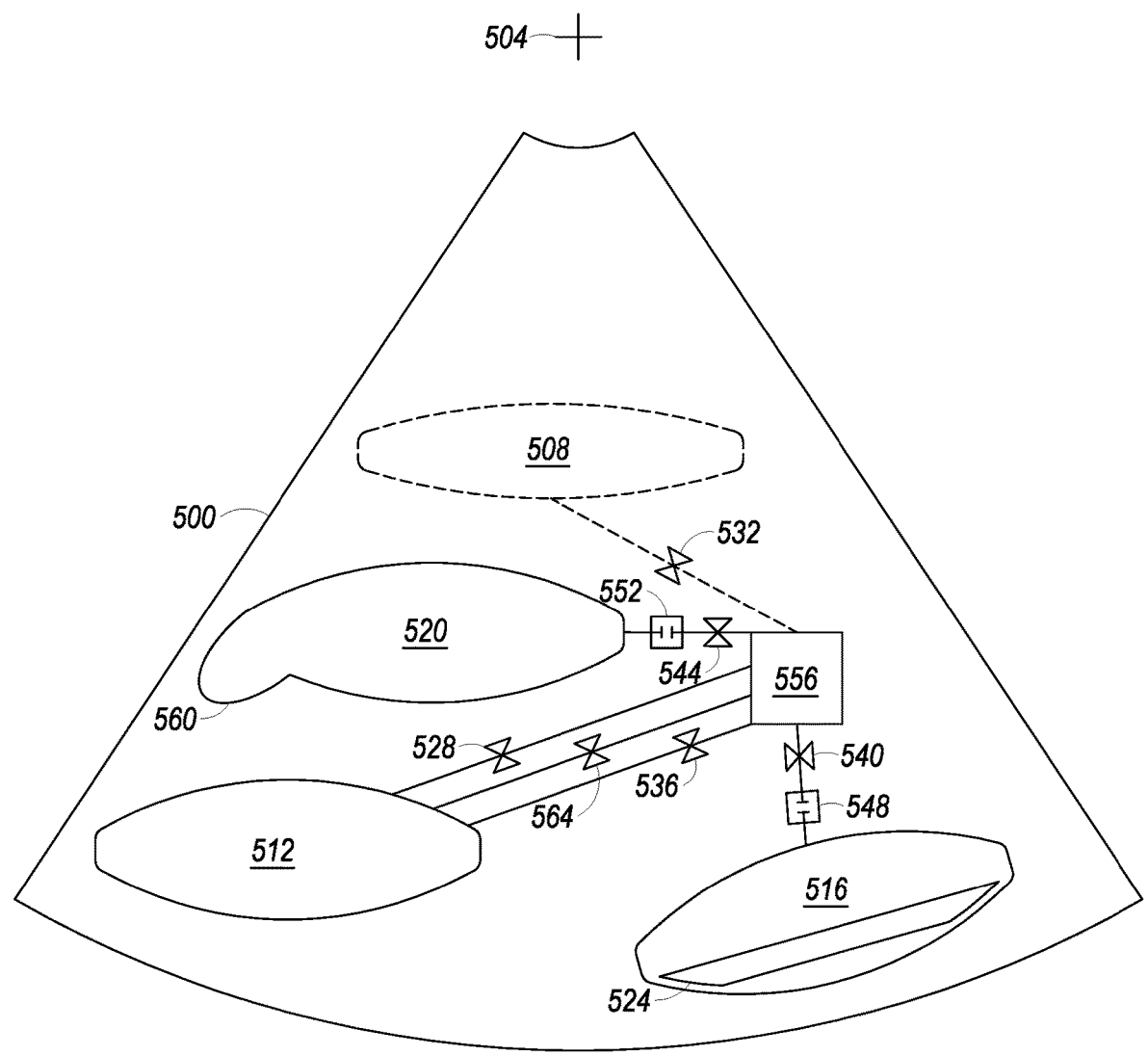
FIG. 5A illustrates a top view of another embodiment of a separation unit.

FIG. 5A illustrates a top view of another embodiment of a separation unit 500. Separation unit 500 may be one of many separation units installed in a centrifuge apparatus, e.g., apparatus 100. When installed in a centrifuge apparatus, separation unit 500 may be rotated about axis of rotation 504. In the embodiment shown in FIG. 5A, separation unit 500 includes chambers (512, 516, and 520) and an optional chamber 508, which may be used in some embodiments. Expressor 524 may assist in transferring liquid to and from chamber 516.

Separation unit 500 also may include valves 528, 532, 536, 540, 544, and 564. Sensors 548 and 552 may be used to detect the various components of the composite liquid. For example, sensors 548 and 552 may be used to help determine when to stop transferring components from one or more chambers, e.g., when a different component is detected. A recess 556 may also be included in separation unit 500 to hold a coupling or manifold that may be part of a bag system (e.g., system 400) mounted in separation unit 500.

As one example of the use of unit 500, a bag system e.g., system 400 may be loaded into separation unit 500. For example, bag 404 may be positioned in chamber 516, bag 412 may be positioned in chamber 520, bag 408 may be positioned in chamber 512, bag 416 may be positioned in chamber 512 or in chamber 508 when the separation unit 500 includes chamber 508 and bag 420 (when used) in chamber 512. In one embodiment, system 400 and unit 500 may be used to separate a unit (a predetermined volume, e.g., from about 250 ml to about 650 ml, such as 500 ml) of whole blood, stored in bag 404, into components. In other embodiments, the volume may be as small as 200 ml or as large as 700 ml.

After system 400 has been loaded, unit 500 may be spun around axis of rotation 504 to create centripetal acceleration. For example, unit 500 may be in an apparatus such as centrifuge apparatus 100 that spins unit 500. The force generated by the centripetal acceleration may be stronger the further away from axis 504. Accordingly, chamber 516 may experience the largest force, followed by chamber 512, chamber 520, and finally chamber 508, which may experience the least amount of force. The centripetal acceleration may increase with the speed of rotation of unit 500 around axis 504.

Unit 500 may be spun around axis of rotation 504 at a first speed to create a first centripetal acceleration. The centripetal acceleration may effect the separation of blood in chamber 516 into components. For example, based on the differences in size and/or density, the blood may be separated in bag 404 into red blood cells, white blood cells, and a plasma/platelet portion or part (e.g., PRP). In embodiments, chamber 516 may be slanted or angled with respect to axis 504. In other words, a distal end of chamber 516 may be further away from the axis of rotation 504 than a proximal end. As a result of the shape/position of chamber 516 and the centripetal acceleration created by spinning unit 500 around axis 504, red blood cells may be at a bottom of bag 404 (in chamber 516), with a layer of white blood cells above the red blood cells, and a layer of platelets/plasma above the layer of white blood cells. In embodiments, all of chambers 508, 512, 516, and 520, may have a similar shape/position with a proximal end closer to the axis of rotation 504 than a distal end, e.g., slanted with respect to axis of rotation 504, to reduce sedimentation time and keep higher density components at the bottom of the container (e.g., bag) during expression.

After the initial separation, valves 540 and 544 may be opened and expressor 524 may be activated to express the platelets/plasma portion (e.g., PRP) out of chamber 516 (and out of bag 404). In embodiments, the platelets/plasma may be expressed from chamber 516 (and out of bag 404) into chamber 520 (and into bag 412). The expression may move a first portion of the plasma (with platelets) from chamber 516 into chamber 520. It is noted that some portion of plasma may remain in chamber 516 with the red blood cells and white blood cells. Sensor 548 may be used to determine when to stop expressing the platelets/plasma from chamber 516. For example, sensor 548 may sense the platelets/plasma as it flows from chamber 516 to chamber 520 and when the presence of white blood cells is sensed, the expressor 524 may be deactivated and valves 548 and 544 closed.

After the platelets/plasma are expressed into chamber 520, the unit 500 may be spun around axis of rotation 504, at a second speed, to create a second centripetal acceleration. In embodiments, unit 500 may be continuously spun during the entire process. In these embodiments, rotating at the second speed may involve ramping up (or down) the speed of unit 500 from a speed at which the unit 500 is rotating. In embodiments, the second centripetal acceleration may be greater than the first centripetal acceleration. In other embodiments, the second centripetal acceleration may be substantially the same as the first centripetal acceleration. However, in yet other embodiments, the second centripetal acceleration may be less than the first centripetal acceleration. As may be appreciated, the strength of the centripetal acceleration may be controlled by how fast the unit 500 is spun around axis of rotation 504.

The second spin may separate the platelets from the plasma in chamber 520. Because of the size and density difference, the platelets may settle toward a bottom of chamber 520 with the plasma on top of the platelets. Also, in chamber 516 (and in bag 404), the second spin may separate additional plasma from the red blood cell and white blood cell layers. Again, because of density difference, the plasma may be on top of the red blood cell and white blood cell layers. Also, the fact that less plasma remains with the platelets, may result in a higher quality platelet product. In some embodiments, it may be desirable to have less plasma in the platelets to reduce transfusion reactions that may result from plasma protein(s) transfused into patients with platelets.

In the embodiment shown in FIG. 5A, chamber 520 includes a platelet pocket 560, e.g., a volume of space where platelets may settle during the second spin. As described above, the plasma/platelets may be in bag 412, which is in chamber 520. Bag 412 may be flexible so that it conforms to the shape of chamber 520, namely it deforms to platelet pocket 560 to allow platelets to settle in the pocket 560 and still be within bag 412. Although FIG. 5A illustrates pocket 560 extending to the top of chamber 520, in some embodiments, the pocket 560 may extend only a portion along the depth of chamber 520. However, in other embodiments, pocket 560 may extend the entire depth of chamber 520.

As illustrated in FIG. 5A, pocket 560 is radially outward from the rest of chamber 520. The position of pocket 560, further radially outward from the axis of rotation 504, ensures that the platelets are held in pocket 560.

Figure 5B:
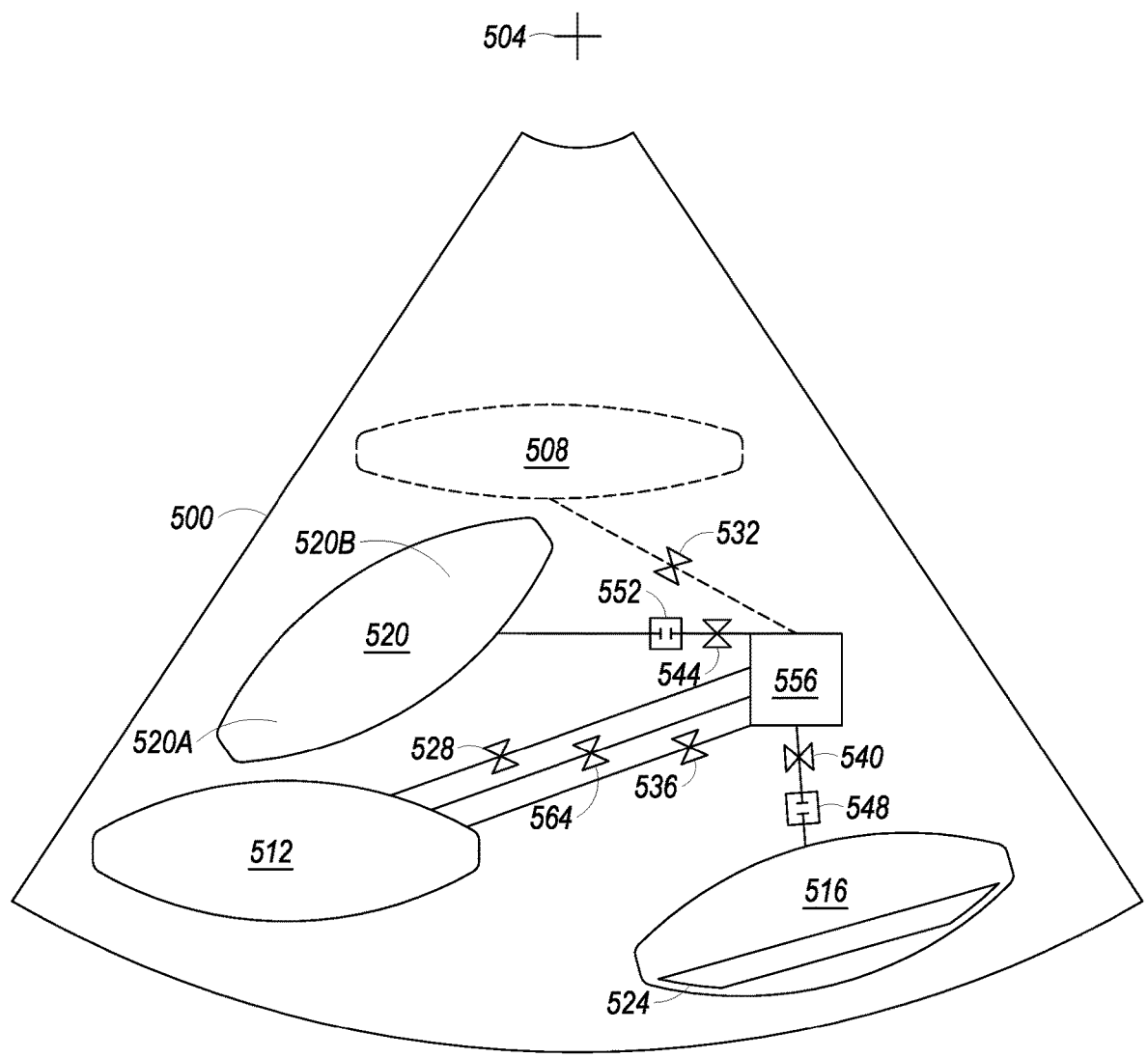
FIG. 5B illustrates a top view of another embodiment of a separation unit.

An alternative embodiment of chamber 520 is shown in FIG. 5B. As shown in FIG. 5B, chamber 520 may be rotated so that a portion 520A of chamber 520 is radially outward from the remaining portion 520B. In these embodiments, portion 520A may act as a pocket for platelets, e.g., as pocket 560, in chamber 520.

Referring back to FIG. 5A, the chambers 520 and 512 of separation unit 500 are positioned so that an expressor may not be necessary to move components from chamber 520 to chamber 512. That is, chamber 512 may be further away from the axis of rotation 504 than chamber 520, so that when unit 500 is spun and valves 528 and 544 opened, components may flow from chamber 520 to chamber 512. In order for components to flow from chamber 520 to chamber 512, the flow path should be "downhill" throughout the entire flow path.

After the second spin, the unit 500 may be spun relatively slowly. The slow spin may be used to move components from chamber 520 into chamber 512 (and into bag 408). As noted above, because of the position of chamber 512, as unit 500 is spun to create centripetal acceleration, plasma may flow (from head height) from chamber 520 into chamber 512. As the plasma is transferred from chamber 520 to chamber 512, the platelets may remain in pocket 560. Sensor 552 may be used to determine when platelets start transferring. For example, sensor 552 may sense the plasma as it flows from chamber 520 to chamber 512 and when the presence of platelets is sensed, valves 528 and 552 may be closed to stop flow of plasma from chamber 520 to chamber 512.

Additionally, expressor 524 may be activated and valve 540 opened to express a third portion of plasma (separated by the second spin) from chamber 516 to chamber 512. In embodiments, this provides a larger volume of plasma than may be conventionally collected from a unit (a predetermined volume, e.g., about 500 ml) of whole blood. As may be appreciated, the second spin allows additional plasma to be separated from the red blood cell and white blood cell layers.

After the third portion of plasma is removed from chamber 516 (and bag 416), valves 540 and 564 may be opened and expressor 524 may be activated to express the layer of white blood cells from chamber 516 (and bag 416) into chamber 512 (and into bag 416). In embodiments that include chamber 508 (with bag 404 in chamber 508), valves 540 and 532 may be opened and expressor 524 activated to express the white blood cells into bag 404. Sensor 548 may be used to determine when to stop expressing the white blood cells from chamber 516. Sensor 548 may sense the white blood cells as they flow from chamber 516 and when the presence of red blood cells is sensed, the expressor 524 may be deactivated and valves 540 and 564 (or 532) closed to stop the flow of components from chamber 516.

In those embodiments that utilize sub-system 460, valves 540 and 536 may be opened and expressor 524 may be activated to express the red blood cells from chamber 516 (and bag 404) through filter 468 and into bag 420 (e.g., in chamber 512). Once the red blood cells have been expressed out of bag 404, valves 540 and 536 may be closed and the expressor 524 may be deactivated.

Figure 6:
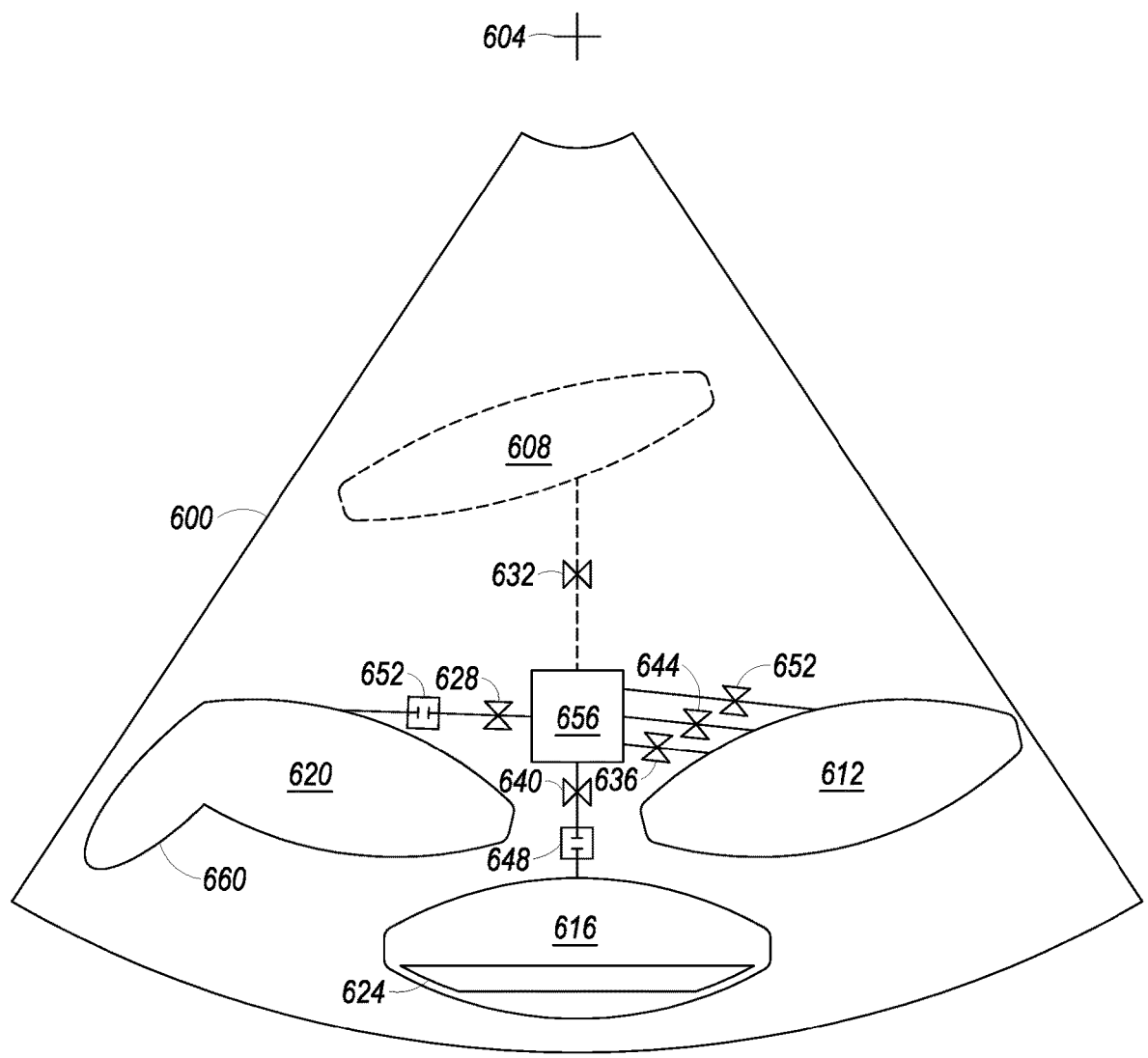
FIG. 6 illustrates a top view of yet another embodiment of a separation unit.

FIG. 6 illustrates a top view of another embodiment of a separation unit 600. Separation unit 600 may be one of many separation units installed in a centrifuge apparatus, e.g., apparatus 100. When installed in a centrifuge apparatus, separation unit 600 may be rotated about axis of rotation 604. In the embodiment shown in FIG. 6, separation unit 600 includes chambers 612, 616, and 620, and optional chamber 608 is some embodiments. Expressor 624 may assist in transferring fluid to and from chamber 616.

Separation unit 600 may also include valves 628, 632, 636, 640, 644 and 652. Sensors 648 and 652 may be used to detect the various components of the composite liquid. For example, sensors 648 and 652 may be used to help determine when to stop transferring components from one or more chambers, e.g., when a different component is detected. A recess 656 may also be included in separation unit 600 to hold a coupling or manifold that may be part of a bag system (e.g., system 400) mounted in separation unit 600.

As one example of the use of unit 600, a bag system, e.g., system 400 may be loaded into separation unit 600. For example, bag 404 may be positioned in chamber 616, bag 412 may be positioned in chamber 620, bag 408 may be positioned in chamber 612, bag 416 may be positioned in chamber 612, and bag 420 in chamber 612. In embodiments where chamber 608 is used, bag 416 may be positioned in optional chamber 608. In one embodiment, system 400 and unit 600 may be used to separate a unit (a predetermined volume, e.g., between about 250 ml and about 650 ml, such as 450 ml) of whole blood, stored in bag 404, into components. In other embodiments, the volume may be as small as 200 ml or as large as 700 ml.

After system 400 has been loaded, unit 600 may be spun around axis of rotation 604 to create centripetal acceleration. For example, unit 600 may be in an apparatus such as centrifuge apparatus 100 that spins unit 600. The force created by the centripetal acceleration may be stronger further away from axis 604. Accordingly, chamber 616 may experience the largest force, followed by chamber 620, and chamber 612, and finally optional chamber 608, which may experience the least amount of force. The centripetal acceleration may increase with the speed of rotation of unit 600 around axis 604. Unit 600 may be spun around axis of rotation 604 at a first speed to create a first centripetal acceleration. The centripetal acceleration may effect the separation of blood in chamber 616 into components. For example, based on the differences in density, the blood may be separated in bag 604 into red blood cells, white blood cells, and a plasma/platelets portion (e.g., PRP). In embodiments, chamber 616 may be slanted or angled with respect to axis 604. In other words, a distal end of chamber 616 may be further away from the axis of rotation 604 than a proximal end. As a result of the shape/position of chamber 616 and the centripetal acceleration created by spinning unit 600 around axis 604, red blood cells may be at a bottom of bag 604, with a layer of white blood cells above the red blood cells, and a layer of platelets/plasma (e.g., PRP) above the layer of white blood cells. The platelets/plasma layer may be at the top. In embodiments, all of chambers 608, 612, 616, and 620, may have a similar shape with a proximal end closer to the axis of rotation 604 than a distal end, e.g., slanted with respect to axis of rotation 604.

After the initial separation, valves 628 and 640 may be opened and expressor 624 may be activated to express the platelets/plasma layer out of chamber 616 (and out of bag 404). In embodiments, the platelets/plasma may be expressed from chamber 616 into chamber 620 (and into bag 412). The expression may move a first portion of the plasma (with platelets) from chamber 616 into chamber 620. It is noted that some portion of plasma may remain in chamber 616 with the red blood cells and white blood cells. Sensor 648 may be used to determine when to stop expressing the platelets/plasma from chamber 616. For example, sensor 648 may sense the platelets/plasma as it flows from chamber 616 to chamber 620 and when the presence of white blood cells is sensed, the expressor 624 may be deactivated and valves 628 and 640 closed.

After the platelets/plasma is expressed into chamber 620, the unit 600 may be spun around axis of rotation 604, at a second speed, to create second centripetal acceleration. In embodiments, the second strength may be greater than the first strength. In other embodiments, the second strength may be substantially the same as the first strength. However, in yet other embodiments, the second strength may be less than the first strength. As may be appreciated, the centripetal acceleration may be controlled by how fast the unit 600 is spun around axis of rotation 604. In embodiments, the unit 600 may be continuously spinning throughout the process. In these embodiments, the speed of unit 600 may be changed to generate the second centripetal acceleration.

The second spin may separate the platelets from the plasma in chamber 620. Because of the size and/or density difference, the platelets may settle toward a bottom of chamber 620 with the plasma on top of the platelets. Also, in chamber 616 (and in bag 404), the second spin may separate additional plasma from the red blood cell and white blood cell layers. Again, because of size and/or density difference, the plasma may be on top of the red blood cell and white blood cell layers.

In the embodiment shown in FIG. 6, chamber 620 includes a platelet pocket 660, e.g., a volume of space where platelets may settle during the second spin. The plasma/platelets may be in bag 412, which is in chamber 620. Bag 412 may be flexible so that it conforms to the shape of chamber 620, namely it deforms to platelet pocket 660 to allow platelets to settle in the pocket 660 and still be within bag 412. In some embodiments, the pocket 660 may extend only a portion along the depth of chamber 620. However, in other embodiments, pocket 660 may extend the entire depth of chamber 620.

In the embodiment shown in FIG. 6, chamber 620 of separation unit 600 is positioned so that an expressor may not be necessary to move components from chamber 620. That is, chamber 616 may be further away from the axis of rotation 604 than chamber 620, so that when unit 600 is spun and valves 628 and 640 opened, components may flow from chamber 620 back to chamber 616.

After the second spin, the unit 600 may be spun and valves 628 and 640 opened. The spinning may be used to move components from chamber 620 back to chamber 616 (and into bag 404). As noted above, because of the position of chamber 616, as unit 600 is spun to create centripetal acceleration, plasma may flow (from head height) from chamber 620 back into chamber 616. Sensor 652 may be used to determine when platelets start transferring. For example, sensor 652 may sense the plasma as it flows from chamber 620 back to chamber 616 and when the presence of platelets is sensed, valves 628 and/or 648 may be closed to stop flow of plasma from chamber 620 to chamber 616.

After the plasma has been moved back to chamber 616, expressor 624 may be activated and valves 640 and 636 opened to express plasma, including a third portion of plasma (separated by the second spin) from chamber 616 to chamber 612. In embodiments, this provides a larger volume of plasma than may be conventionally collected from a unit (e.g., about 450 ml) of whole blood. As may be appreciated, the second spin allows additional plasma to be separated from the red blood cell and white blood cell layers. Also, the fact that less plasma remains with the platelets, may result in a higher quality platelet product. In some embodiments, having less plasma in the platelets, may reduce transfusion reactions that may result from plasma protein(s) transfused into patients with platelets.

In some embodiments, some plasma may be accurately pushed back to chamber 620 from chamber 616 using the expresser 624. These embodiments allow for a controlled amount of plasma to be added back to the platelets.

Finally, after the plasma is removed from chamber 616 (and bag 404), valves 640 and 644 may be opened and expressor 624 may be activated to express the layer of white blood cells from chamber 616 (and bag 404) into chamber 612 (and into bag 416). In those embodiments where bag 404 is in chamber 408, valves 640 and 632 may be opened to express the white blood cells into bag 404 in chamber 608. Sensor 648 may be used to determine when to stop expressing the white blood cells from chamber 616. Sensor 648 may sense the white blood cells as they flow from chamber 616 and when the presence of red blood cells is sensed, the expressor 624 may be deactivated and valves 640 and 644/632 closed.

In those embodiments that utilize sub-system 460, valves 640 and 652 may be opened and expressor 624 may be activated to express the red blood cells from chamber 616 (and bag 404) through filter 468 and into bag 420 (e.g., in chamber 612). Once the red blood cells have been expressed out of bag 404, valves 640 and 652 may be closed and the expressor 624 may be deactivated.

It is noted that the separation units 200, 500, and 600 described above include features that are provided for illustrative purposes. Other embodiments may provide for different designs. For example, other embodiments may utilize fewer valves, different chamber positions, different number of chambers. Some embodiments may combine features of separation units 200, 500, and 600. The present invention is therefore not limited to the embodiments described above.

Figure 7:
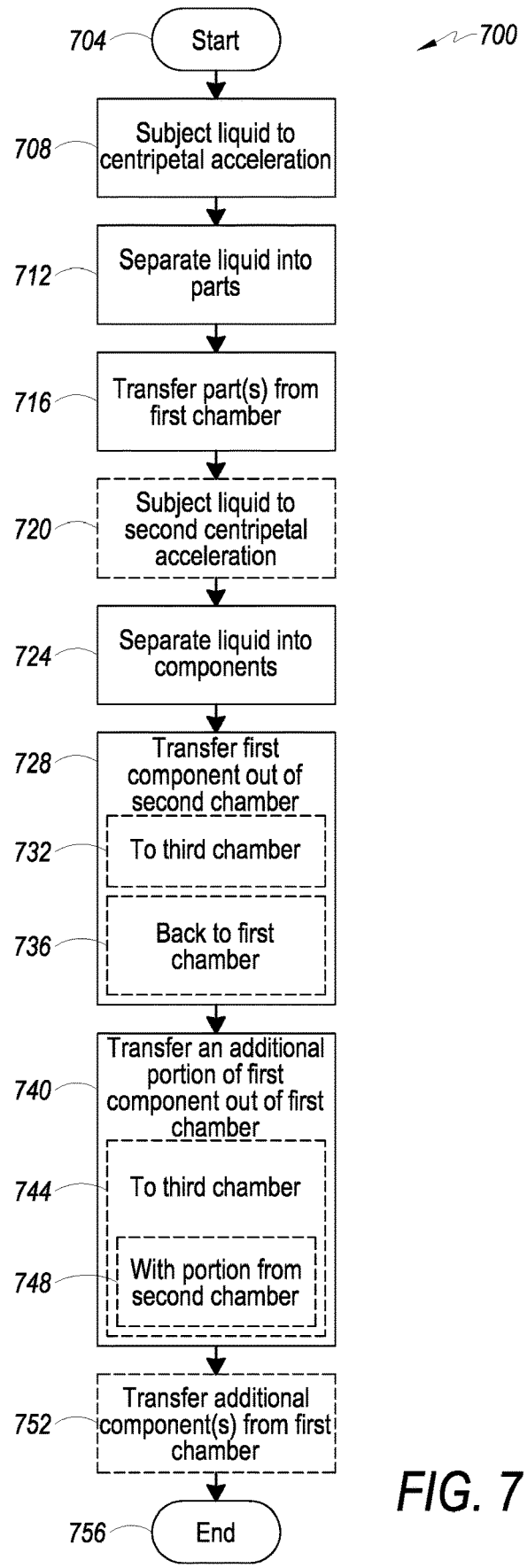
FIG. 7 illustrates a flow chart of a method for separating components of a composite fluid according to an embodiment.
Figure 8:
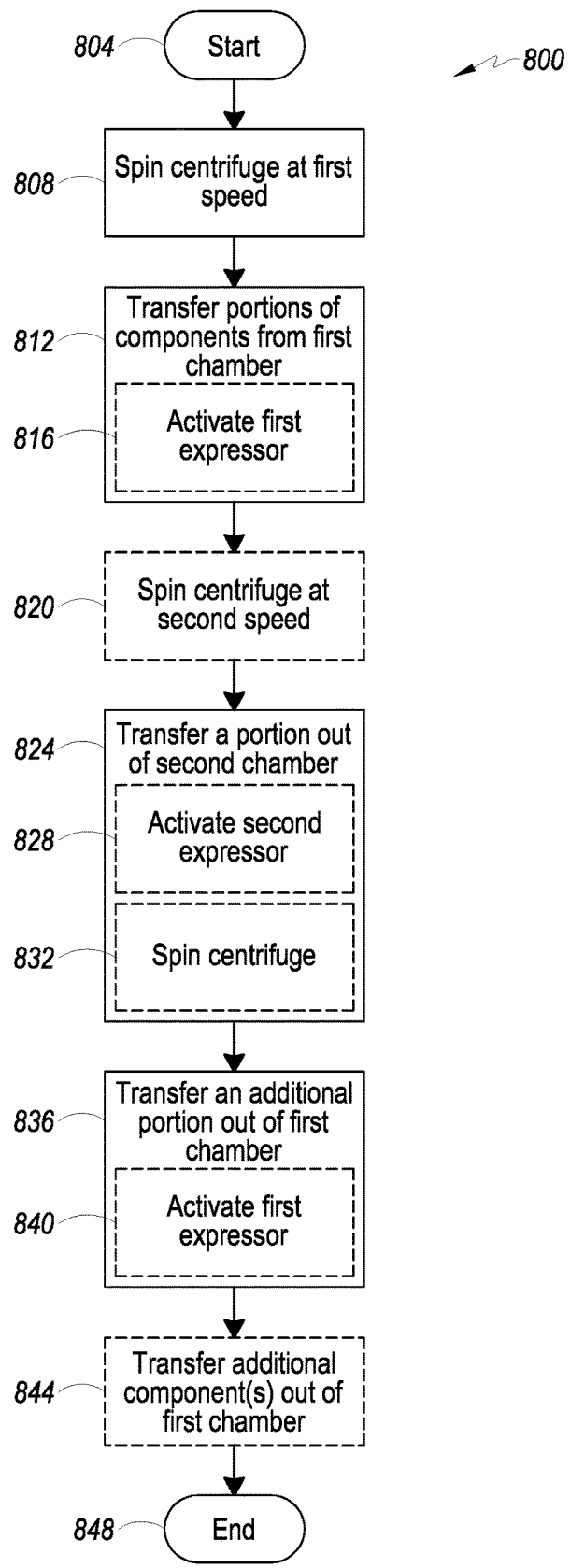
FIG. 8 illustrates a flow chart of a method for separating components of a composite fluid according to another embodiment.

FIGS. 7 and 8 illustrate flow charts 700 and 800 for processes of separating components from a volume of composite fluids, e.g., liquids. In one embodiment, the composite liquid may be whole blood, and the components may be one or more of plasma, platelets, white blood cells, buffy coat, red blood cells, and combinations thereof. Although the steps in flow charts 700 and 800 may be described below as performed by a computing device and/or a separation apparatus (e.g., centrifuge apparatus, such as centrifuge apparatus 100), this is done merely for illustrative purposes, and flow charts 700 and 800 are not limited to being performed in a specific way, e.g., by any specific device, apparatus, or system.

Flow 700 starts at 704. At step 708, a liquid, e.g., whole blood, is subjected to a first centripetal acceleration. In embodiments, the liquid may be in a container such as a bag that may be part of a bag system, e.g., system 400 (FIG. 4). In embodiments, the bag system may be loaded onto a separation unit that is part of a separation system. In embodiments, the liquid may be spun around an axis of rotation, creating centripetal acceleration. The volume of liquid may be separated into parts at step 712. As may be appreciated, the centripetal acceleration may separate the liquid into parts based on differences in size and/or density. Each part may be composed of different components. As one example, when the liquid is whole blood, the components may include plasma, platelets, white blood cells, and red blood cells. Each of the parts may include one or more of the components. For example, a first part may include plasma and platelets, and a second part may include white blood cells and red blood cells.

At step 716, a first part, which may include a first component and a second component, may be transferred from a first chamber. In embodiments, step 716 may involve transferring the first part from a first chamber to a second chamber. In embodiments, the chambers may be part of a separation unit, such as separation units 200, 500, and/or 600. Step 716 may in embodiments involve transferring a first part from one chamber (e.g., chamber 216, 516, and/or 616) to a second chamber (e.g., chamber 220, 520, and/or 620).

As may be appreciated, step 716 may be performed by any means that can move materials from one location or another. As one example, an expressor (e.g., 224, 524, and/or 624) may be used to press or squeeze a bag in the first chamber. The expressor may be operated using systems such as electromechanical, hydraulic, pneumatic, vacuum, centrifugal, or combinations of these types of systems.

After step 716, the liquid (including the transferred part(s)) may be subjected to a second centripetal acceleration at optional step 720. In embodiments, the liquid may be spun around an axis of rotation, creating second centripetal acceleration. In embodiments, the second centripetal acceleration may be greater than the first centripetal acceleration of step 708. For example, the first centripetal acceleration may be used as part of a soft spin for an initial separation of components. A hard spin may occur as part of step 720, indicating that the second centripetal acceleration may be greater than the first centripetal acceleration. As may be appreciated, the second centripetal acceleration may provide greater separation of components. In other embodiments, the second centripetal acceleration may be less than the first centripetal acceleration. In other embodiments, step 720 may not be performed, and the liquid may be subjected to a continuous centripetal acceleration that remains substantially the same during the process.

As may be appreciated, when optional step 720 is performed, the second centripetal acceleration may additionally separate the liquid (including the transferred part) into components based on differences in size and/or density at step 724. The first part may be further separated into a first component and a second component. The second part, which may have remained in the first chamber, may be further separated into a first component, a third component, and a fourth component.

For example, when the volume of liquid is whole blood, the first part may include plasma and platelets. At step 724, plasma and platelets may separate in the second chamber as a result of the second centripetal acceleration. The second part (which may have remained in the first chamber) may include white blood cells, red blood cells, and some plasma. At step 724, plasma, white blood cells, and red blood cells may additionally separate in the second chamber as a result of the second centripetal acceleration.

After step 724, flow 700 passes to step 728 where a component, e.g., the first component, is transferred out of the second chamber. In embodiments, step 728 may involve one or more sub-steps. For example, step 728 may involve transferring a component from the second chamber to a third chamber, namely optional sub-step 732. In other embodiments, step 728 may involve transferring the component from the second chamber back to the first chamber, namely optional sub-step 736.

As may be appreciated, step 728 may be performed by any device that can move materials from one location to another. As one example, an expressor (e.g., 224, 524, and/or 624) may be used to press or squeeze a bag in the second chamber. The expressor may be operated using systems such as electromechanical, hydraulic, pneumatic, vacuum, centrifugal, or combinations of these types of systems.

In another embodiment, the transferring may be accomplished by the position of chambers and opening valves. For example, as illustrated above with respect to FIGS. 5A, 5B, and 6, chambers may be positioned so that centripetal acceleration may be used to move components from one chamber (e.g., 520 and/or 620) to another chamber (e.g., 512 and/or 616) by having one chamber closer to the axis of rotation than the other chamber and opening valves to allow fluid communication between them.

After step 728, flow 700 passes to step 740 where an additional portion of a component, e.g., the first component, is transferred out of the first chamber. In embodiments, step 740 may involve one or more sub-steps. For example, step 740 may involve transferring the portion of the component from the first chamber to a third chamber, namely optional sub-step 744. In other embodiments, at step 728 a portion of the first component may have been transferred from the second chamber to the first chamber. In these embodiments, sub-step 744 may involve an additional, optional sub-step 748 of transferring the component (previously transferred from the second chamber back to the first chamber) with the additional portion of the component out of the first chamber.

As may be appreciated, step 740 may be performed by any device that can move materials from one location or another. As one example, an expressor (e.g., 224, 524, and/or 624) may be used to press or squeeze a bag in the first chamber. The expressor may be operated using systems such as electromechanical, hydraulic, pneumatic, vacuum, centrifugal, or combinations of these types of systems. In another embodiment, the transferring may be accomplished by opening valves. For example, the chambers may be positioned so that centripetal acceleration may move components from one chamber (e.g., 520 and/or 620) to another chamber (e.g., 512 and/or 616) by having the first chamber closer to the axis of rotation than the third chamber.

An optional step 752 may be performed to transfer a third and/or fourth component(s), e.g., white blood cells and/or red blood cells from the first chamber. In embodiments, when step 752 may be performed to transfer a third component from the first chamber, this may result in isolation of the fourth component, e.g., red blood cell in the first chamber. Flow 700 then ends at 756.

Flow 800 in FIG. 8 illustrates a process for separating a composite fluid into components. In embodiments, flow 800 may be performed by a computer system (e.g., computer system 900) that is part of and controls a separation system such as centrifuge apparatus 100. Flow 800 starts at 804. At step 808, a centrifuge is spun at a first speed. In embodiments, several steps may be performed prior to step 808. For example, a bag system that includes a volume of composite fluid, e.g., whole blood, may be loaded into a first chamber of the centrifuge, e.g., bag system 400 (FIG. 4). Other bags in the bag system may be loaded into other chambers. In embodiments, the step of spinning the centrifuge may create centripetal acceleration that results in separation of the volume into components.

Flow 800 passes from step 808 to step 812 where portions of the components are transferred from a first chamber to a second chamber. In embodiments, step 812 may involve one or more sub-steps. For example, as part of transferring portions of the components, step 816 may involve a sub-step 816 of activating an expressor (e.g., 224, 524, and/or 624) to transfer the components out of a first chamber, e.g., express the components by pressing against a bag in the first chamber to squeeze components out of the bag. The expressor may be part of a larger system, for example: electromechanical, hydraulic, pneumatic, vacuum, centrifugal, or combinations of these systems.

In embodiments where the composite fluid is whole blood, step 812 may involve transferring platelets and a portion of the plasma (e.g., a first portion) from the first chamber. The platelets and plasma may have been separated during the spinning of the centrifuge at step 808. White blood cells, red blood cells, and some plasma may remain in the first chamber after step 812.

Flow 800 passes from 812 to optional step 820 where the centrifuge is spun at a second speed. In embodiments, the second speed may be an increase from a current speed of the centrifuge. In embodiments, step 820 may create a second centripetal acceleration that results in additional separation of the components in the first chamber and the second chamber. For example, when the composite fluid is whole blood, step 820 may result in the platelets being separated from the plasma in the second chamber. In the first chamber, step 820 may result in additional plasma being separated from the white blood cells and red blood cells.

Also, step 820 may result in platelets with less plasma. In embodiments, having less plasma in the platelets, may reduce transfusion reactions that may result from plasma protein(s) transfused into patients with platelets.

In embodiments, the second speed may be faster than the first speed. For example, the first speed may be referred to as a soft spin for an initial separation of components. A hard spin may occur as part of step 820, indicating that the centrifuge may be spun at a faster speed than the first speed. As may be appreciated, the faster spin may create greater centripetal acceleration that provides greater separation of components. In other embodiments, the second speed may be slower than the first speed. In some embodiments where step 820 is not performed, the centrifuge may remain spinning at a substantially constant speed throughout the process.

At step 824, portions of the components are transferred from the second chamber. In embodiments, step 824 may involve one or more sub-steps. For example, as part of transferring portions of the components, step 824 may involve a sub-step 828 of activating a second expressor (e.g., 228) to transfer components out of the second chamber, e.g., express the components by pressing against a bag in the second chamber to squeeze components out of the bag. Similar to the expressor that may be used, in embodiments for performing step 812, the second expressor may be part of a larger system, for example: electromechanical, hydraulic, pneumatic, vacuum, centrifugal, or combinations of these systems.

In other embodiments, step 824 may involve opening valves and having centripetal acceleration drain the components out of the second chamber to another location. This may be accomplished, in some embodiments, by positioning the second chamber closer to an axis of rotation of the centrifuge than the chamber to which the components are transferred. For example, as illustrated in FIG. 5A, a third chamber (e.g., chamber 512) may be positioned further from an axis of rotation than the second chamber (e.g., chamber 520). When a centrifuge is spun, components may flow from the second chamber to a third chamber.

In embodiments where the composite fluid is whole blood, step 824 may involve transferring plasma (e.g., a second portion) from the second chamber. The plasma may have been further separated during the spinning of the centrifuge at optional step 820. Platelets may remain in the second chamber (with some plasma).

In embodiments, step 824 may involve transferring the component from the second chamber into a third chamber. In other embodiments, step 824 may involve transferring the component from the second chamber back to the first chamber.

After step 824, flow 800 passes to step 836 where an additional portion of a component is transferred out of the first chamber. In embodiments, step 836 may involve one or more sub-steps. For example, sub-step 840 may involve activating the first expressor to transfer the additional portion of the component out of the first chamber, e.g., express the component by pressing against the bag in the first chamber to squeeze the component out of the bag.

In embodiments where the composite fluid is whole blood, step 836 may involve transferring plasma (e.g., third portion) from the first chamber. The plasma may have been further separated (e.g., from white blood cells and red blood cells) during the spinning of the centrifuge at optional step 820.

In embodiments, as noted above, step 824 may involve transferring the component from the second chamber into a third chamber. In these embodiments, step 836 may involve transferring the additional portion of the component (e.g., a third portion) out of the first chamber to the third chamber.

As noted above, in other embodiments step 824 may involve transferring the component from the second chamber back to the first chamber. In these embodiments, step 836 may involve transferring the additional portion (e.g., third portion) of the component out of the first chamber with the portion transferred into the first chamber at step 824 (e.g., second portion).

In embodiments, flow 800 may pass to step 844, where an additional component is transferred out of the first chamber.

For example, when flow 800 is used to separate whole blood, step 844 may be performed to transfer a white blood cell layer and/or red blood cells from the first chamber. Flow 800 then ends at 848.

Although flows 700 and 800 have been described with steps listed in a particular order, the present disclosure is not limited thereto. In other embodiments, steps may be performed in different order, in parallel, or any different number of times, e.g., before and after another step. Also, as indicated above, flows 700 and 800 include some optional steps/sub-steps. However, those steps above that are not indicated as optional should not be considered as essential to the invention, but may be performed in some embodiments of the present invention and not in others.

Figure 9:
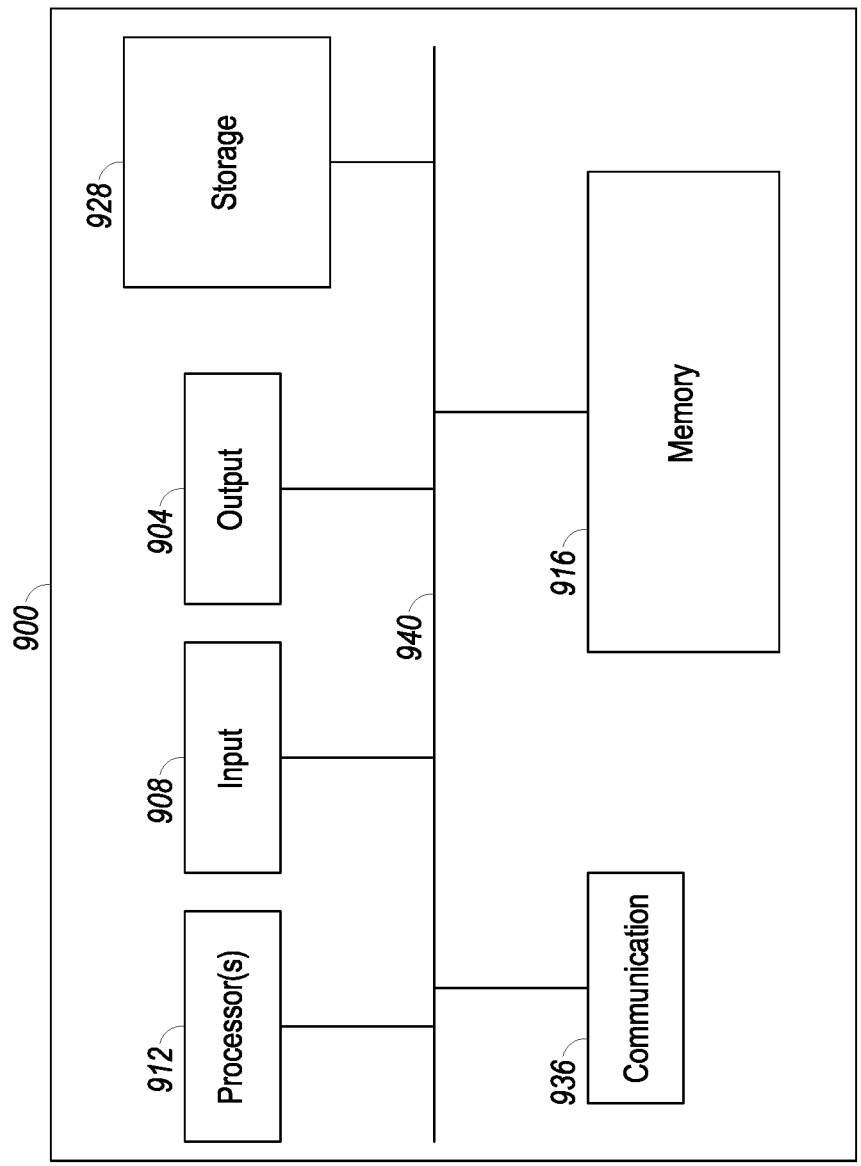
FIG. 9 illustrates components of a computing system that may be used to implement embodiments.

FIG. 9 illustrates example components of a basic computer system 900 upon which embodiments of the present invention may be implemented. For example, apparatus 100 (FIG. 1) may incorporate features of the basic computer system 900 shown in FIG. 9. Also, steps/sub-steps described above with respect to flows 700 and 800 may be performed in whole or in part by features of a computer system, such as system 900.

Computer system 900 includes output device(s) 904, and input device(s) 908. Output device(s) 904 may include, among other things, one or more displays, including CRT, LCD, LED, and/or plasma displays. Output device(s) 904 may also include printers, speakers, etc. Input device(s) 908 may include, without limitation, a keyboard, touch input devices, a mouse, voice input device, scanners, etc.

Basic computer system 900 may also include one or more processor(s) 912 and memory 916. In embodiments, the processor(s) 912 may be a general-purpose processor(s) operable to execute processor executable instructions stored in memory 916. Processor(s) 912 may include a single processor or multiple processors, according to embodiments. Further, in embodiments, each processor may be a single core or a multi-core processor, having one or more cores to read and execute separate instructions. The processors may include, in embodiments, general purpose processors, application specific integrated circuits (ASICs), field programmable gate arrays (FPGAs), and/or other integrated circuits.

The memory 916 may include any tangible storage medium for short-term or long-term storage of data and/or processor executable instructions. The memory 916 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 928 may be any long-term data storage device or component. Storage 928 may include one or more of the devices described above with respect to memory 916. Storage 928 may be permanent or removable.

Computer system 900 also includes communication devices 936. Devices 936 allow system 900 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 900 are shown in FIG. 9 as connected by system bus 940. It is noted, however, that in other embodiments, the components of system 900 may be connected using more than a single bus.

It will be apparent to those skilled in the art that various modifications and variations can be made to the methods and structure of the present invention without departing from its scope. Thus it should be understood that the invention is not limited to the specific embodiments or examples given. Rather, the invention is intended to cover modifications and variations.

While example embodiments and applications of the present invention have been illustrated and described, it is to be understood that the invention is not limited to the precise configuration described above. Various modifications, changes, and variations apparent to those skilled in the art may be made in the arrangement, operation, and details of the methods and systems of the present invention.

What is claimed is:

1. A system for separating components of a composite fluid, the system comprising:
    a centrifuge;
    a plurality of separation units positioned in the centrifuge, each of the separation units comprising:
        a first chamber comprising a first expressor;
        a second chamber positioned closer to an axis of rotation than the first chamber, wherein the second chamber comprises a second expressor;
        a third chamber;
        a first valve controlling flow from the first chamber; and
        a second valve controlling flow from the second chamber; and
    a memory storing processor-executable instructions that, when said instructions are executed, perform a method comprising:
        spinning the centrifuge at a first speed to separate at least a first component, a second component, and a third component of the composite fluid;
        transferring a portion of the first component and the second component from the first chamber to the second chamber using the first expressor;
        spinning the centrifuge at a second speed; and
        transferring a second portion of the first component out of the second chamber; and
        transferring a third portion of the first component out of the first chamber using the first expressor.

2. The system of claim 1, wherein the transferring of the second portion of the first component out of the second chamber is performed using the second expressor.

3. The system of claim 1, wherein the transfer of the second portion of the first component out of the second chamber is performed using centripetal acceleration.

4. The system of claim 1, wherein the step of transferring a second portion of the first component out of the second chamber transfers the second portion of the first component from the second chamber to the third chamber.

5. The system of claim 1, wherein the step of transferring a second portion of the first component out of the second chamber transfers the second portion of the first component from the second chamber back to the first chamber.

6. The system of any one of claim 1, wherein the step of transferring a third portion of the first component out of the first chamber transfers the third portion of the first component from the first chamber to the third chamber.

7. The system of claim 1, wherein the third chamber is closer to the axis of rotation than the second chamber.

8. The system of claim 1, wherein the composite fluid comprises whole blood.

9. The system of claim 8, wherein the first component comprises plasma and the second component comprises platelets.

10. The system of claim 9, wherein the second speed is faster than the first speed.

11. A method for separating components of a composite fluid, the method comprising:
    subjecting a volume of the composite fluid comprising a first component, a second component, and a third component to a first centripetal acceleration;
    separating the volume of composite fluid into two parts;
    transferring a first part comprising a portion of the first component and the second component from a first chamber by action of a first expressor connected to said first chamber to a second chamber;
    subjecting the transferred first part to a second centripetal acceleration thereby separating the first and second components;
    returning the first component out of the second chamber by action of a second expressor coupled to said second chamber back to the first chamber; and
    transferring said returned first component and an additional portion of the first component out of the first chamber.

12. The method of claim 11, wherein the transferring the returned first component and the additional portion of the first component out of the first chamber further comprises, transferring the returned first component and the additional portion from the first chamber to a third chamber.

13. The method of claim 11, wherein, the second centripetal acceleration is greater than the first centripetal acceleration.

14. The method of claim 11, wherein the composite fluid comprises whole blood.

* * * * *